(12) United States Patent
Furar et al.

(10) Patent No.: US 6,960,768 B2
(45) Date of Patent: Nov. 1, 2005

(54) METHOD FOR DETERMINING THE DURABILITY OF A COMPOSITE STRUCTURE

(75) Inventors: John M. Furar, Pittsburgh, PA (US); Robyn E. McMillan, Allison Park, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 187 days.

(21) Appl. No.: 10/361,430

(22) Filed: Feb. 10, 2003

(65) Prior Publication Data

US 2004/0155189 A1 Aug. 12, 2004

(51) Int. Cl.$^7$ ............................................. G01N 21/35
(52) U.S. Cl. ................................................. 250/339.01
(58) Field of Search .................................... 250/339.01

(56) References Cited

U.S. PATENT DOCUMENTS

| | | | |
|---|---|---|---|
| 5,389,219 A | 2/1995 | Zwack et al. ............ 204/181.1 |
| 6,184,528 B1 * | 2/2001 | DiMarzio et al. ...... 250/339.08 |
| 2004/0026622 A1 * | 2/2004 | DiMarzio et al. ........ 250/341.8 |
| 2004/0151843 A1 * | 8/2004 | Weingartz ................... 427/553 |

FOREIGN PATENT DOCUMENTS

EP   1 229 321 A2   1/2002

OTHER PUBLICATIONS

Larry P. Haack, Ann M. Straccia, Jered J. Dziadosz and Joseph W. Holubka, Ultra–Low–Angle Cross–Sectional Microtoming Technique for the Chemical Characterization of Bonding Interphases in Layered Polymeric Systems, 2002, Proceedings of the Annual Meetings of the Adhesion Society, 25$^{th}$ Annual, Presented Orally, not Published.

Ann M. Straccia, Larry P. Haack, Jered J. Dziadosz, Joseph W. Holubka, XPS Characterization of Bonding Interphases in Paint Systems Following Ultra–Low–Angle Cross–Sectional Microtoming, 2002, Proceedings of the Annual Meeting of the Adhesion Society; 25$^{th}$ Annual, pp.: 487–489.

John A. Reffner, Pamala A. Martoglio, United Microscopy and Spectroscopy, Jun. 2002, American Laboratory Int. Scientific Communication Inc., Shelton CT., vol. 32, No. 13, pp.: 41–84.

Phillip V. Yaneff, Karlis Adamsons, Rose A. Ryntz, Dottie Britz, Structure/Property Relationships in Flexible Alkoxysilane Automotive Coatings, Oct. 2002, Journal of Coatings Technology, FSCT, Blue Bell, PA, vol. 74, No. 933, pp.: 135–141.

* cited by examiner

*Primary Examiner*—Constantine Hannaher
(74) *Attorney, Agent, or Firm*—Deborah M. Altman (57) ABSTRACT

A method is provided for predicting the durability of a composite structure, such as a composite polymeric coating. The method includes obtaining a sample of a first (reference) composite structure and analyzing at least one layer of the structure for indications of degradation. The sample can be obtained by low angle microtomy. Degradation values and a degradation slope of the first composite structure can be defined. One or more degradation values for a second composite structure can be obtained and the durability of the second composite structure can be predicted by comparing the degradation slope of the second composite structure to the degradation slope of the first composite structure.

21 Claims, 2 Drawing Sheets

METHOD FOR DETERMINING THE DURABILITY OF A COMPOSITE STRUCTURE

BACKGROUND OF THE INVENTION

1. Field of the Invention

This invention relates generally to a method for determining or predicting the durability of a multi-layer composite structure, such as a multi-layer polymeric coating, and, more particularly, to a method for determining the effects of changes in composition and/or processing parameters on the durability of a composite structure.

2. Technical Considerations

Composite structures can take many forms. One example of a composite structure is a multi-layer polymeric coating. The durability of such composite coatings is an important feature to many consumers. By "durability" is meant the ability of the coating to withstand various weathering conditions, such as rain, humidity, sunlight, heat, cold, and various chemicals without failure of the coating. Coating "failure" can take the form of delamination of the coating from the substrate or from a previously applied coating layer on which it is deposited. Other types of coating failure could include blistering, loss of color, loss of adhesion, and various other changes in the mechanical and/or chemical properties of the coating that would make the coating less desirable for its intended use.

In an effort to improve or alter coating characteristics and/or to streamline production processes, coating producers may change the composition of a particular coating and/or one or more of the processing parameters under which the coating is formed. However, even minor changes in the coating composition and/or the processing parameters can impact upon the durability of the subsequent coating. In the past, the impact on coating durability of any such changes would be ascertained by subjecting the modified coating to a weathering atmosphere, such as an outdoor atmosphere, for an extended period of time to test the durability of the modified coating. This process could take many months, if not years, to complete to provide an accurate assessment of the coating durability.

As an alternative to this time consuming process, accelerated weathering procedures have been developed to attempt to predict coating durability in a shorter length of time. These accelerated procedures typically rely upon exposing the coating to artificial conditions, such as short wavelength energy, high intensity light, and high humidity, in order to accelerate coating degradation. The coating durability is then estimated based upon the results of exposure to these artificial conditions. However, many of the artificial tests still take months to complete. Additionally, coating durability estimates based on such artificial conditions may not correlate well to coating durability under actual use conditions.

Recently, methods for estimating coating durability which can be done in a shorter length of time than prior conventional tests have been developed. One such method is disclosed in European Patent Application EP 1,229,321. In this method, a set of coatings is exposed to the same ambient outdoor conditions for the same period of time. The exposed coatings are then subjected to a chemiluminescence test. The results of the chemiluminescence test for one selected coating are compared to the chemiluminescence results for at least one other coating of the set to estimate coating durability based on the coating chemiluminescence. However, this method cannot estimate a time until coating failure. Additionally, this method is based on measuring the light signal that arises from heat-induced decomposition of a species when the coating is exposed to outdoor conditions. Should such species not be present or should the type of failure attempted to be quantified not be based on the presence of such species, this method would not be applicable.

Therefore, it would be advantageous to provide a method of predicting the durability of a composite structure, such as a composite polymeric coating, that eliminates or reduces at least some of the problems currently encountered.

SUMMARY OF THE INVENTION

A method is provided for predicting the durability of a composite structure, such as but not limited to a composite polymeric coating. The method includes obtaining a sample of a first (reference) composite structure and analyzing at least one layer of the structure for indications of degradation. For example, the at least one layer can include one or more under layers or outer layers of the composite structure or the substrate upon which the one or more under layers or outer layers are located. Indications of degradation can include indications of degradation caused by photo-oxidation, hydrolysis, and thermal degradation, just to name a few. In one embodiment, the sample is obtained by conducting low angle microtomy of the first composite structure. In one particular embodiment, degradation values of at least one layer, for example, an under layer, can be measured over time and a degradation slope of the first coating can be defined. One or more degradation values for a second composite structure can then be obtained and a degradation slope of the second composite structure defined. The durability of the second composite structure compared to the durability of the first composite structure can then be predicted by comparing the degradation slope of the second composite structure (second slope) to the degradation slope of the first composite structure (first slope). If the second slope is less than the first slope, then the second composite structure is predicted to have a higher durability than the first composite structure.

In another aspect of the invention, a failure value can be defined for the first composite structure. In one embodiment, the failure value can correspond to a degradation value at which the first composite structure is no longer deemed suitable for its intended purpose, e.g., a degradation value at which the first composite structure delaminates. The time until the second composite structure reaches the failure value can then be estimated from the second slope prior to actual failure.

DESCRIPTION OF THE PREFERRED EMBODIMENTS

As used herein, spatial or directional terms, such as "left", "right", "inner", "outer", "above", "below", "top", "bottom", and the like, relate to the invention as it is shown in the drawing figures. However, it is to be understood that the invention may assume various alternative orientations and, accordingly, such terms are not to be considered as limiting. Further, as used herein, all numbers expressing dimensions, physical characteristics, processing parameters, quantities of ingredients, reaction conditions, and the like, used in the specification and claims are to be understood as being modified in all instances by the term "about". Accordingly, unless indicated to the contrary, the numerical values set forth in the following specification and claims are approximations that may vary depending upon the desired properties sought to be obtained by the present invention. At the very least, and not as an attempt to limit the application of the doctrine of equivalents to the scope of the claims, each numerical value should at least be construed in light of the number of reported significant digits and by applying ordinary rounding techniques. Moreover, all ranges disclosed herein are to be understood to include the beginning and ending range values and to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 5.5 to 10. Further, as used herein, the terms "deposited over", "applied over", or "provided over" mean deposited or provided on but not necessarily in contact with the surface. For example, a coating composition "deposited over" a substrate does not preclude the presence of one or more other coating films of the same or different composition located between the deposited coating and the substrate. Also, as used herein, the term "polymer" is meant to refer to oligomers and both homopolymers and copolymers. Molecular weights, whether number average molecular weights (Mn) or weight average molecular weights (Mw), are those obtained by gel permeation chromatography using polystyrene standards in an art-recognized manner. As used herein, the term "composite structure" refers to a structure having one or more layers or films. The terms "layer" or "film" refer to a region of a composite structure having a desired or selected composition. A "coating", "coating system", or "coating stack" is composed of one or more "coating films" or "coating layers". Any reference "incorporated by reference" herein is to be understood to be incorporated in its entirety.

An exemplary composite structure will first be described and then a method of predicting the durability of a composite structure in accordance with the invention will be described. The exemplary composite structure described below is a polymeric coating deposited on a substrate (with the substrate understood to be a part of the composite structure). However, it is to be understood that the specific composite structure, e.g., coating stack, described hereinafter is simply one exemplary composite structure for which the durability can be estimated using the methods of the invention. It is to be understood that the invention is not limited to the particularly disclosed coating stack. Examples of other composite structures than can be utilized in the practice of the invention include, but are not limited to, polymeric coatings on plastic substrates, polymeric coatings on metal substrates, a composite of two or more plastic or polymeric layers, or organic or inorganic coatings or combinations, just to name a few.

Figure 1:
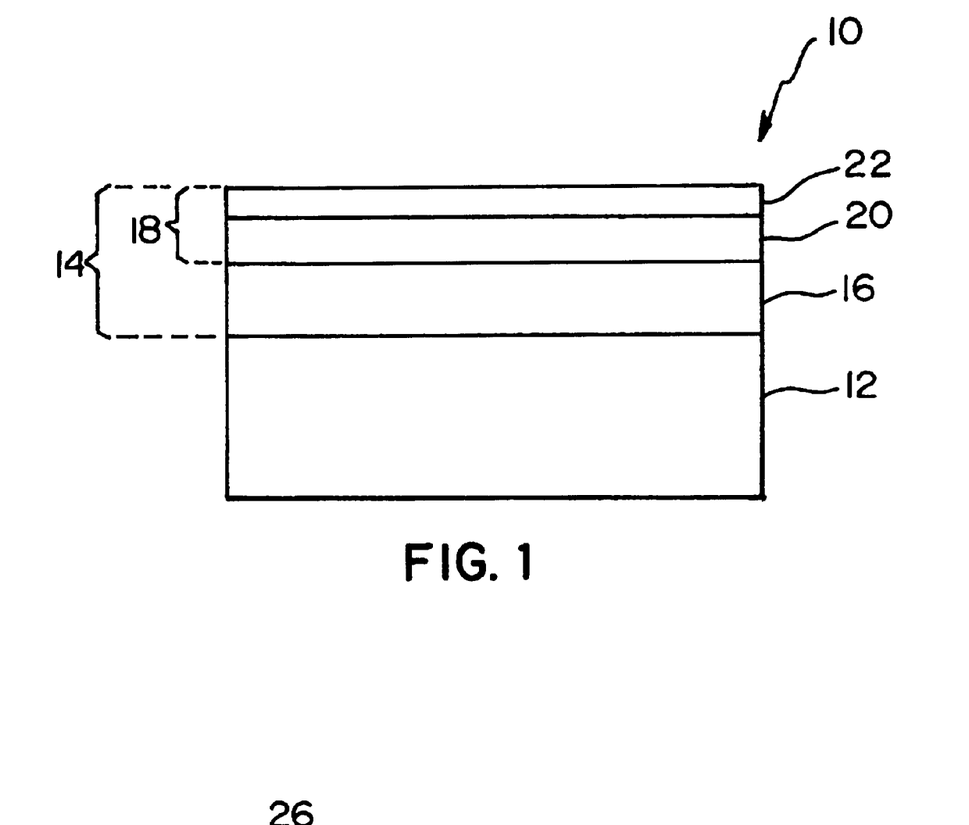
FIG. 1 is a side, sectional view (not to scale) of an exemplary coating for which the durability can be predicted.

A composite structure in the form of a coated article 10 is shown in FIG. 1. As described in more detail below, the article 10 includes a substrate 12 having a coating stack 14 deposited over at least a portion of the substrate 12. In the exemplary illustrated article 10, the coating stack 14 includes at least one under layer 16 and at least one outer layer, such as a topcoat 18, deposited over the under layer 16. The topcoat 18 can include at least one basecoat 20 or basecoat layer with at least one clearcoat 22 or clearcoat layer deposited over the basecoat 20. As used herein, the term "under layer" refers to a coating region or layer located between the substrate and a subsequently deposited "outer layer".

In the broad practice of the invention, the substrate 12 can be of any material having any desired characteristics. Useful substrates that can be utilized include, but are not limited to, metal substrates, polymeric substrates such as thermoset materials and thermoplastic materials, glass substrates, and combinations thereof. Useful metal substrates include ferrous metals such as iron, steel, and alloys thereof, non-ferrous metals such as aluminum, zinc, magnesium and alloys thereof, and combinations thereof. The substrate 12 can be formed from cold rolled steel, electrogalvanized steel such as hot dip electro-galvanized steel or electrogalvanized iron-zinc steel, aluminum or magnesium.

Useful thermoset materials include polyesters, epoxides, phenolics, and polyurethanes such as reaction injected molding urethane (RIM) thermoset materials and mixtures thereof. Useful thermoplastic materials include thermoplastic polyolefins such as polyethylene and polypropylene, polyamides such as nylon, thermoplastic polyurethanes, thermoplastic polyesters, acrylic polymers, vinyl polymers, polycarbonates, acrylonitrile-butadiene-styrene (ABS) copolymers, EPDM rubber, copolymers, and mixtures thereof.

Useful glass substrates include conventional untinted soda-lime-silica-glass, i.e., "clear glass", tinted or otherwise colored glass, borosilicate glass, leaded glass, tempered, untempered, annealed, or heat-strengthened glass. The glass may be of any type, such as conventional float glass or flat glass, and may be of any composition having any optical properties, e.g., any value of visible transmission, ultraviolet transmission, infrared transmission, and/or total solar energy transmission.

In one embodiment, the substrate 12 can be a component used to fabricate automotive vehicles, including but not limited to automobiles, trucks, and tractors. The substrate 12 can have any shape, such as in the form of automotive body components such as bodies (frames), hoods, doors, fenders, bumpers and/or trim for automotive vehicles, just to name a few.

In one non-limiting embodiment, the under layer 16 can be a conventional primer or primer surfacer or can be an electrocoat, such as an electrodeposited anticorrosion layer. For example, the under layer 16 can be a primer or primer surfacer formed from a liquid, powder slurry, or powder (solid) coating composition applied to the surface of the substrate 12 by any suitable coating method well known to those skilled in the automotive coating art, for example, by dip coating, direct roll coating, reverse roll coating, curtain coating, spray coating, brush coating, and combinations thereof.

The primer or primer surfacer coating composition can comprise one or more film-forming materials, volatile materials and, optionally, coloring pigments. Additionally, the primer coating composition, whether liquid, powder slurry, or powder, can comprise one or more thermosetting film-forming materials, such as polyurethanes, acrylics, polyesters, epoxies, and crosslinking materials. The primer coating components can include urethane compositions, which may include filler material such as flow/wetting agents, barium sulfate and/or magnesium silicate for solids content, silicone oils for mar resistance, fumed silicas, and the like. Non-limiting examples of useful primers are disclosed in U.S. Pat. Nos. 4,971,837; 5,492,731; and 5,262,464, which are herein incorporated by reference.

Alternatively, the under layer 16 can be formed from one or more electrodepositable coating compositions (such as POWER-PRIME®, ENVIRO-PRIME®, or DURA-PRIME® coating systems commercially available from PPG Industries, Inc. of Pittsburgh, Pa.). Useful electrodeposition methods and electrodepositable coating compositions include conventional anionic or cationic electrodepositable coating compositions, such as epoxy, acrylic, or polyurethane-based coatings. Examples of suitable electrodepositable coatings are discussed in U.S. Pat. Nos. 4,933,056; 5,530,043; 5,760,107; 5,389,219; and 5,820,987, and U.S. patent application Ser. Nos. 10/010,437 and 10/005,830, which are all herein incorporated by reference.

In one particular embodiment, the under layer 16 can be an electrodepositable coating deposited from a composition comprising a resinous phase dispersed in an aqueous medium. The resinous phase can comprise (1) one or more ungelled, cationic resins or polymers, typically an active hydrogen group-containing, cationic amine salt group-containing polymer, which are electrodepositable on a cathode; and (2) one or more at least partially blocked aliphatic polyisocyanate curing agents.

Cationic polymers suitable for use in the electrodepositable coating compositions, typically as the main film-forming polymer, can include any of a number of cationic polymers well known in the art so long as the polymers are "water dispersible", i.e., adapted to be solubilized, dispersed or emulsified in water. Such polymers comprise cationic functional groups to impart a positive charge.

By "ungelied" is meant the resins are substantially free of crosslinking and have an intrinsic viscosity when dissolved in a suitable solvent as determined, for example, in accordance with ASTM-D1795 or ASTM-D4243. The intrinsic viscosity of the reaction product is an indication of its molecular weight. A gelled reaction product, on the other hand, since it is of essentially infinitely high molecular weight, will have an intrinsic viscosity too high to measure. As used herein, a reaction product that is "substantially free of crosslinking" refers to a reaction product that has a weight average molecular weight (Mw), as determined by gel permeation chromatography, of less than 1,000,000.

Suitable examples of such cationic film-forming resins can include active hydrogen-containing, cationic polymers selected from one or more of a polyepoxide polymer, an acrylic polymer, a pplyurethane polymer, a polyester polymer, mixtures thereof, and copolymers thereof, for example a polyester-polyurethane polymer. The resin (1) can comprise a polyepoxide polymer, or a mixture of a polyepoxide polymer and an acrylic polymer. As aforementioned, the polymers which are suitable for use as the cationic resin (1) comprise active hydrogens as curing reaction sites. The term "active hydrogen" refers to those groups which are reactive with isocyanates as determined by the Zerewitnoff test as is described in the JOURNAL OF THE AMERICAN CHEMICAL SOCIETY, Vol. 49, page 3181 (1927). In one embodiment, the active hydrogens are derived from hydroxyl groups, primary amine groups, and/or secondary amine groups.

Any of a variety of polyepoxides known in the related art can be used to form the cationic resin (1). Examples of polyepoxides which are suitable for this purpose include those having a 1,2-epoxy equivalency greater than one, and typically two; that is, polyepoxides that have on average two epoxide groups per molecule. Such polyepoxide polymers can include the polyglycidyl ethers of cyclic polyols, for example polyhydric phenols, such as Bisphenol A. These polyepoxides can be prepared by etherification of polyhydric phenols with an epihalohydrin or dihalohydrin, such as epichlorohydrin or dichlorohydrin in the presence of alkali. Non-limiting examples of suitable polyhydric phenols include 2,2-bis-(4-hydroxyphenyl)propane, 1,1-bis-(4-hydroxyphenyl)ethane, 2-metyl-1,1-bis-(4hydroxyphenyl) propane, 2,2-(4-hydroxy-3-tertiarybutylphenyl)propane, and bis-(2-hydroxynaphthyl)methane Besides polyhydric phenols, other cyclic polyols can be used to prepare the polyglycidyl ethers of cyclic polyol derivatives. Examples of such cyclic polyols include alicyclic polyols, such as cycloaliphatic polyols, for example 1,2-cyclohexanediol, 1,4-cyclohexanediol, 1,2-bis-(hydroxymethyl)cyclohexane, 1,3-bis-(hydroxymethyl) cyclohexane, and hydrogenated Bisphenol A.

The polyepoxides can be chain-extended with a polyether or a polyester polyol. Examples of suitable polyether polyols and conditions for chain extension are disclosed in U.S. Pat. No. 4,468,307. Examples of polyester polyols for chain extension are disclosed in U.S. Pat. No. 4,148,772.

Other suitable polyepoxides can be produced similarly from novolak resins or similar polyphenols. Such polyepoxide resins are described in U.S. Pat. Nos. 3,663,389; 3,984,299; 3,947,338; and 3,947,339. Additional polyepoxide resins which are suitable for use informing the cationic resin (1) include those described in U.S. Pat. Nos. 4,755,418; 5,948,229; and 6,017,432.

Suitable acrylic polymers from which the active hydrogen-containing, cationic salt group-containing polymer may be derived can include copolymers of one or more alkyl esters of acrylic acid or methacrylic acid, optionally together with one or more other polymerizable ethylenically unsaturated monomers. Suitable alkyl esters of acrylic acid or methacrylic acid include methyl methacrylate, ethyl methacrylate, butyl methacrylate, ethyl acrylate, butyl acrylate, and 2-ethyl hexyl acrylate. Suitable other copolymerizable ethylenically unsaturated monomers include nitriles such acrylonitrile and methacrylonitrile, vinyl and vinylidene halides such as vinyl chloride and vinylidene fluoride, and vinyl esters such as vinyl acetate. Acid and anhydride functional ethylenically unsaturated monomers such as acrylic acid, methacrylic acid or anhydride, itaconic acid, maleic acid or anhydride, or fumaric acid may be used. Amide functional monomers including acrylamide, methacrylamide, and N-alkyl substituted (meth)acrylamides are also suitable. Vinyl aromatic compounds, such as styrene and vinyl toluene, can be used so long as photodegradation resistance of the polymer and the resulting electrodeposited coating is not compromised.

Functional groups, such as hydroxyl and amino groups, can be incorporated into the acrylic polymer by using functional monomers such as hydroxyalkyl acrylates and methacrylates or aminoalkyl acrylates and methacrylates. Epoxide functional groups (for conversion to cationic salt groups) may be incorporated into the acrylic polymer by using functional monomers, such as glycidyl acrylate and methacrylate, 3,4-epoxycyclohexylmethyl(meth)acrylate, 2-(3,4-epoxycyclohexyl)ethyl(meth)acrylate, or allyl glycidyl ether. Alternatively, epoxide functional groups may be incorporated into the acrylic polymer by reacting carboxyl groups on the acrylic polymer with an epihalohydrin or dihalohydrin, such as epichlorohydrin or dichlorohydrin. The acrylic polymer can be prepared by traditional free radical initiated polymerization techniques, such as solution or emulsion polymerization, as known in the art using suitable catalysts which include organic peroxides and azo type compounds and, optionally, chain transfer agents such as alpha-methyl styrene dimer and tertiary dodecyl mercaptan. Additional acrylic polymers which are suitable for forming the active hydrogen-containing, cationic amine salt group-containing resin (1) which is used in the electrodepositable compositions of the present invention include those resins described in U.S. Pat. Nos. 3,455,806 and 3,928,157, herein incorporated by reference.

Mixtures of the polymers described above also can advantageously be used. In one embodiment, the cationic resin (1) can comprise a mixture of a cationic polyepoxide polymer and a cationic acrylic polymer.

The active hydrogen-containing resin (1) can comprise cationic amine salt groups derived from pendant and/or terminal amino groups. By "terminal and/or pendant" is meant that primary and/or secondary amino groups are present as a substituent which is pendant from or in the terminal position of the polymeric backbone, or, alternatively, is an end-group substituent of a group which is pendant and/or terminal from the polymer backbone. In other words, the amino groups from which the cationic amine salt groups are derived are not within the polymeric backbone.

The pendant and/or terminal amino groups can have the following structures (I) or (II):

wherein R represents H or $C_1$ to $C_{18}$ alkyl; $R^1$, $R^2$, $R^3$, and $R^4$ are the same or different and each independently represents H or $C_1$ to $C_4$ alkyl; and X and Y can be the same or different and each independently represents a hydroxyl group or an amino group.

By "alkyl" is meant alkyl and aralkyl, cyclic or acyclic, linear or branched monovalent hydrocarbon groups. The alkyl groups can be unsubstituted or substituted with one or more heteroatoms, for example, non-carbon, non-hydrogen atoms such as one or more oxygen, nitrogen, or sulfur atoms.

The pendant and/or terminal amino groups represented by structures (I) and (II) above can be derived from a compound selected from the group consisting of ammonia, methylamine, diethanolamine, diisopropanolamine, N-hydroxyethyl ethylenediamine, diethylenetriamine, and mixtures thereof. One or more of these compounds is reacted with one or more of the above described polymers, for example, a polyepoxide polymer, where the epoxy groups are ring-opened via reaction with a polyamine, thereby providing terminal amino groups and secondary hydroxyl groups.

In one particular embodiment, the cationic salt group-containing polymer can contain amine salt groups which are derived from one or more pendant and/or terminal amino groups having the structure (II) above, such that when the electrodepositable coating composition is electrodeposited and cured, at least two electron-withdrawing groups are bonded in the beta-position relative to substantially all of the nitrogen atoms present in the cured electrodeposited coating. In a further embodiment of the invention, when the electrodepositable coating composition is electrodeposited and cured, three electron-withdrawing groups are bonded in the beta-position relative to substantially all of the nitrogen atoms present in the cured electrodeposited coating. By "substantially all" of the nitrogen atoms present in the cured electrodeposited coating is meant at least 65 percent, and typically 90 percent, of all nitrogen atoms present in the cured electrodeposited coating which are derived from the amine used to form the cationic amine salt groups.

In one embodiment, the curing agent (2) can comprise one or more at least partially blocked aliphatic polyisocyanates. The curing agents employed in cationic electrodeposition compositions can be blocked aliphatic polyisocyanates. The aliphatic polyisocyanates can be fully blocked as described in U.S. Pat. No. 3,984,299 column 1, lines 1 to 68; column 2; and column 3, lines 1 to 15, or partially blocked and reacted with the polymer backbone as described in U.S. Pat. No. 3,947,338 column 2, lines 65 to 68; column 3; and column 4, lines 1 to 30. By "blocked" is meant that the isocyanate groups have been reacted with a compound such that the resultant blocked isocyanate group is stable to active hydrogens at ambient temperature but reactive with active hydrogens in the film-forming polymer at elevated temperatures, usually between 90° C. and 200° C. In one embodiment, the polyisocyanate curing agent is a fully-blocked polyisocyanate with substantially no free-isocyanate groups.

In one embodiment, the polyisocyanate curing agent (2) can be at least partially blocked with at least one blocking agent selected from a 1,2-alkane diol, for example 1,2-propanediol, a 1,3-alkane diol, for example 1,3-butanediol, a benzylic alcohol, for example, benzyl alcohol, an allylic alcohol, for example, allyl alcohol, caprolactam, a dialkylamine, for example dibutylamine, and mixtures thereof. In a further embodiment of the present invention, the polyisocyanate curing agent (2) is at least partially blocked with at least one 1,2-alkane diol having three or more carbon atoms, for example 1,2-butanediol.

The basecoat 20 can be a composite basecoat formed by one or more layers. The basecoat 20 can be formed from a liquid, e.g., waterborne, coating material. As used herein, the term "waterborne" means that the solvent or carrier fluid for the coating material primarily or principally comprises water. The basecoat material can comprise a film-forming material or binder, volatile material and can optionally include one or more pigments. For example, the basecoat material can comprise a crosslinkable coating composition comprising at least one thermosettable film-forming material, such as acrylics, polyesters (including alkyds), polyurethanes and epoxies, and at least one crosslinking material. Thermoplastic film-forming materials such as polyolefins also can be used.

Suitable acrylic polymers include copolymers of one or more of acrylic acid, methacrylic acid, and alkyl esters thereof, such as methyl methacrylate, ethyl methacrylate, hydroxyethyl methacrylate, butyl methacrylate, ethyl acrylate, hydroxyethyl acrylate, butyl acrylate, and 2-ethylhexyl acrylate, optionally together with one or more other polymerizable ethylenically unsaturated monomers including vinyl aromatic compounds such as styrene and vinyl toluene, nitriles such as acrylontrile and methacrylonitrile, vinyl and vinylidene halides, and vinyl esters such as vinyl acetate. Other suitable acrylics and methods for preparing the same are disclosed in U.S. Pat. No. 5,196,485 at column 11, lines 16–60, which are incorporated herein by reference.

Polyesters and alkyds are other examples of resinous binders useful for preparing the basecoating composition. Such polymers can be prepared in a known manner by condensation of polyhydric alcohols, such as ethylene glycol, propylene glycol, butylene glycol, 1,6-hexylene glycol, neopentyl glycol, trimethylolpropane and pentaerythritol, with polycarboxylic acids such as adipic acid, maleic acid, fumaric acid, phthalic acids, trimellitic acid or drying oil fatty acids.

Polyurethanes also can be used as the resinous binder of the basecoat. Useful polyurethanes include the reaction products of polymeric polyols such as polyester polyols or acrylic polyols with a polyisocyanate, including aromatic diisocyanates such as 4,4'-diphenylmethane diisocyanate, aliphatic diisocyanates such as 1,6-hexamethylene diisocyanate, and cycloaliphatic diisocyanates such as isophorone diisocyanate and 4,4'-methylene-bis(cyclohexyl isocyanate).

Suitable crosslinking materials include aminoplasts, polyisocyanates, polyacids, polyanhydrides, and mixtures thereof. Useful aminoplast resins are based on the addition products of formaldehyde, with an amino- or amido-group carrying substance. Condensation products obtained from the reaction of alcohols and formaldehyde with melamine, urea or benzoguanamine are most common. Useful polyisocyanate crosslinking materials include blocked or unblocked polyisocyanates such as those discussed above for preparing the polyurethane. Examples of suitable blocking agents for the polyisocyanates include lower aliphatic alcohols such as methanol, oximes such as methyl ethyl ketoxime, and lactams such as caprolactam.

The basecoat material also can comprise one or more other volatile materials, such as organic solvents and/or amines. Non-limiting examples of useful solvents which can be included in the basecoat material, in addition to any provided by other coating components, include aliphatic solvents such as hexane, naphtha, and mineral spirits; aromatic and/or alkylated aromatic solvents such as toluene, xylene, and SOLVESSO 100; alcohols such as ethyl, methyl, n-propyl, isopropyl, n-butyl, isobutyl and amyl alcohol, and m-pyrol; esters such as ethyl acetate, n-butyl acetate, isobutyl acetate and isobutyl isobutyrate; ketones such as acetone, methyl ethyl ketone, methyl isobutyl ketone, diisobutyl ketone, methyl n-amyl ketone, and isophorone, glycol ethers and glycol ether esters such as ethylene glycol monobutyl ether, diethylene glycol monobutyl ether, ethylene glycol monohexyl ether, propylene glycol monomethyl ether, propylene glycol monopropyl ether, ethylene glycol monobutyl ether acetate, propylene glycol monomethyl ether acetate, and dipropylene glycol monomethyl ether acetate. Useful amines include alkanolamines.

Other additives, such as UV absorbers, hindered amine light stabilizers, rheology control agents or surfactants, can be included in the basecoat material, if desired. Additionally, the basecoat material can include color pigments or coloring agents to provide the basecoat material with a desired color. Non-limiting examples of useful color pigments include iron oxides, lead oxides, carbon black, titanium dioxide, and colored organic pigments such as phthalocyanines. The basecoat material can also include effect pigments, such as mica flakes, aluminum flakes, bronze flakes, coated mica, nickel flakes, tin flakes, silver flakes, copper flakes, and combinations thereof.

Examples of waterborne basecoat materials include those disclosed in U.S. Pat. Nos. 4,403,003; 5,401,790; and 5,071,904, which are incorporated by reference herein. Also, waterborne polyurethanes such as those prepared in accordance with U.S. Pat. No. 4,147,679 can be used as the resinous film former in the basecoat materials, which is incorporated by reference herein. Suitable film formers for organic solvent-based basecoats are disclosed in U.S. Pat. No. 4,220,679 at column 2, line 24 through column 4, line 40 and U.S. Pat. No. 5,196,485 at column 11, line 7 through column 13, line 22, which are incorporated by reference herein.

The clearcoat 22 can be deposited from a liquid, powder slurry (powder suspended in a liquid) or powder (solid) material, as desired. The clearcoat material can be a crosslinkable coating comprising one or more thermosettable film-forming materials and one or more crosslinking materials such as are discussed above. Useful film-forming materials include epoxy-functional film-forming materials, acrylics, polyesters and/or polyurethanes, as well as thermoplastic film-forming materials such as polyolefins can be used. The clearcoat material can include additives such as are discussed above for the basecoat. If the clearcoat material is a liquid or powder slurry, volatile material(s) can be included. The clearcoat material can be a tinted material, e.g., comprising about 3 to about 5 weight percent of coloring pigment on a basis of the total weight of the clearcoat material.

The clearcoat material can be a crosslinkable coating comprising at least one thermosettable film-forming material and at least one crosslinking material, although thermoplastic film-forming materials such as polylefins can be used. A non-limiting example of a waterborne clearcoat is disclosed in U.S. Pat. No. 5,098,947 (incorporated by reference herein) and is based on water-soluble acrylic resins. Useful solvent borne clearcoats are disclosed in U.S. Pat. Nos. 5,196,485 and 5,814,410 (incorporated by reference herein) and include epoxy-functional materials and polyacid curing agents. Suitable powder clearcoats are described in U.S. Pat. No. 5,663,240 (incorporated by reference herein) and include epoxy functional acrylic copolymers and polycarboxylic acid crosslinking agents, such as dodecanedioic add. The amount of the clearcoat material applied to the substrate can vary based upon such factors as the type of substrate and intended use of the substrate, i.e., the environment in which the substrate is to be placed and the nature of the contacting materials.

Figure 2:
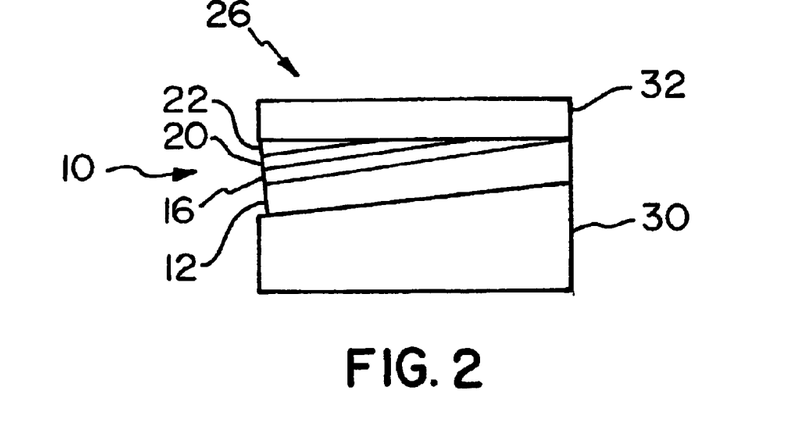
FIG. 2 is a side view (not to scale) of an ultra-low-angle cross-sectional microtoming (ULACSM) device.

Having described an exemplary composite structure in the form of the coated article 10, an exemplary method of predicting the durability of a composite structure, e.g., the durability of the coated article 10, will now be described. In one exemplary method, a first or reference composite structure (e.g., a coated article 10 having a coating stack 14) is subjected to weathering conditions for a period of time sufficient to cause the composite structure to fail. As used herein, the terms "fail" or "failure" mean the point at which the composite structure, e.g., the coating, is no longer suitable for its intended purpose. Such failure could take the form of blistering or de-lamination, just to name a few. During this weathering process, the composite structure is periodically sampled. In one embodiment, this sampling can be done by ultra-low-angle cross-sectional microtoming (ULACSM) of the composite structure to obtain a sample, e.g., coating sample. FIG. 2 schematically shows an exemplary microtome apparatus 26. A general description of low-angle microtome technique is described in "Ultra-low-angle Cross-sectional Microtoming Technique for the Chemical Characterization of Bonding Interfaces in Layered Polymeric Systems" presented at the 25$^{th}$ Annual Adhesive Society Meeting (2002) and herein incorporated by reference.

As shown in FIG. 2, the coated article 10 is placed on an angled base 30 and a section of the composite structure (in this particular example a section of the coating stack 14) is removed by the blade 32 of a conventional low-angle microtome. One suitable microtome is a model SM2500E heavy-duty sliding microtome manufactured by Leica Microsystems. The angle of the composite structure relative to the microtome blade 32 (microtoming angle) is set sufficiently low to provide relatively wide samples of at least some of the layers forming the composite structure (e.g., at least some of the coating layers of the coating stack 14 and/or the substrate 12). For example, the microtoming angle can be less than 5°, such as less than 4°, such as less than 3°, such as less than 2°, such as less than 1°, such as in the range of greater than 0° to less than 1°, such as in the range of 0.1° to 0.5°, such as in the range of 0.2° to 0.4°.

Upon removal of the microtomed section (sample), the sample can be analyzed using conventional analytical techniques. Suitable techniques include, but are not limited to, microscopy techniques such as infrared microscopy, Raman microprobe, ultraviolet microscopy, scanning electron microscopy/energy dispersive x-ray spectroscopy, and atomic force microscopy. Alternatively, surface analytical techniques can be used, such as secondary ion mass spectrometry, time of flight-secondary ion mass spectrometry, x-ray photoelectron spectroscopy, and auger electron spectroscopy. In one particular embodiment, the microtomed sample is examined using infrared microscopy to examine the under layer 16 portion of the sample for indications of degradation. A degradation value (DV) can be defined as follows.

When the infrared spectra of the under layer 16 portion of the sample has been obtained, the OH, NH, and CH peak areas of the spectra can be integrated and the ratio of the OH, NH to CH areas calculated. The initial value for this ratio taken from an unexposed panel (at time t=0) can be subtracted from subsequently measured values at subsequent times (t=x) as shown in equation 1 below:

$$DV = \left[\frac{OH, NH}{CH}\right]_{t=x} - \left[\frac{OH, NH}{CH}\right]_{t=0}$$

Figure 3:
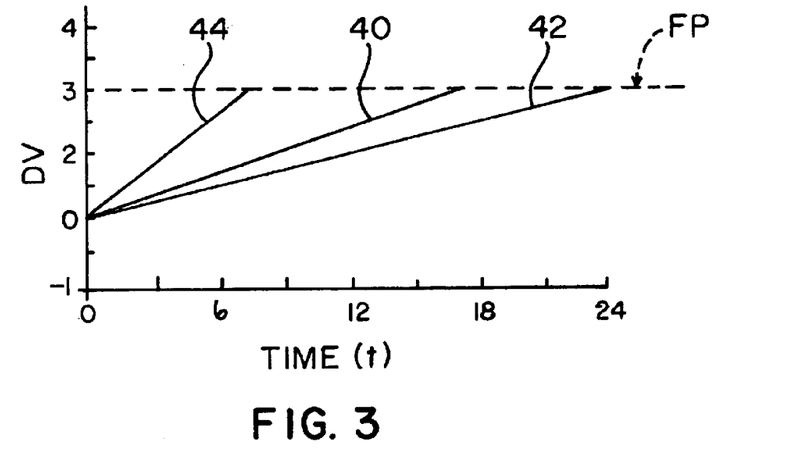
FIG. 3 is an exemplary graph of degradation value (DV) versus time for purposes of explaining the general concepts of the invention.

The difference between the initial value and the subsequently measured value is defined as the degradation value (DV). The DV can then be plotted versus exposure time. An exemplary graph of DV versus exposure time for a reference composite structure is shown in FIG. 3. As shown in FIG. 3, the plotted DV values for the reference structure can be approximated by a straight line 40, with the slope of this line defining the degradation rate of the under layer 16 of the reference structure.

In addition to the degradation rate, a degradation failure point (FP) can be defined for the reference structure. For example, the failure point (FP) could be the point where the coating blisters. Alternatively, the failure point could be defined as the point where the reference structure delaminates, e.g., the topcoat 18 separates from the under layer 16 or the under layer 16 separates from the substrate 12. It has been surprisingly discovered that composite structures having pigmented and unpigmented topcoats of the same or similar chemical composition except for pigment amount can fail between adjacent layers at the same or about the same failure point. Therefore, the reference structure, e.g., coating, can be a structure having a very transparent, i.e., low pigment-containing, topcoat. By "very transparent" is meant having a visible light transparancy of greater than 80 percent. The lack or reduced amount of pigment allows more solar energy to pass through the topcoat 18 and impact upon the under layer(s) 16 in a shorter length of time than would be expected with a more highly pigmented topcoat 18. Thus, the initial or reference degradation rate and failure point for a non-pigmented reference coating can be obtained in a shorter length of time than would be possible with a more pigmented coating.

Once this reference composite structure or coating has been evaluated, other composite structures having changed or modified chemical compositions, structural differences (such as differences in layer thickness or composition), or composite structures formed under different processing parameters than the reference structure can be prepared and the modified structures evaluated for durability as described above. However, since the DV values and degradation rate have already been obtained for the reference structure, only a few DV values for the modified structure need be obtained. Once sufficient DV values for the modified structure have been obtained to permit drawing a best fit line through these points, the slope of the line for the modified structure can be compared to that of the reference structure to determine whether the modifications improved or degraded the durability of the composite structure. Looking at FIG. 3, modified coating 42 illustrates a structure having improved durability versus the reference structure (40). By "improved durability" is meant that the slope of the line for the structure 42 is less than the slope of the line 40 for the reference structure. Similarly, structure 44 in FIG. 3 indicates a modified structure that has lower durability than that of the reference structure. While structures 42 and 44 can represent changes in chemical composition from the reference structure, these structures could also represent changes in the processing conditions or processing parameters of structures having the same chemical composition as the reference structure. For example, these structures 42 and 44 could represent structures, e.g., polymeric coatings, processed at differing processing parameters, such as curing temperature or oven conditions. Or, structures 42 and 44 could represent structures having one or more differing layers (e.g., topcoats) or having differing layer thicknesses. Thus, the impact of modifications in the compositions and/or process parameter changes on the durability of the composite structure can be quickly and more easily determined than with previously known systems.

Illustrating the invention is the following example which, however, is not to be considered as limiting the invention to its details.

EXAMPLE 1

Test Panel Preparation:

A conventional electrodepositable coating composition as described in U.S. Pat. No. 5,389 219, Example 2, was electrodeposited onto 4 inch by 12 inch (10 cm by 30 cm) zinc-phosphated galvanized steel test panels commercially available from ACT Laboratories, Inc. as APR23834(B) (E60 EZG 60G, two sided with C700 C18 phosphate and rinse). The conventional electrodepositable coating composition was electrodeposited on the substrate under conditions that provided a substantially continuous film having a thickness of approximately 1 mil (25.4 microns). The electrodeposited test panel was thermally cured at 375° F. (191° C.) for 60 minutes in a gas-fired oven.

The test panels were then topcoated with a series of solvent-based basecoat and clearcoat systems designed to permit transmission of various amounts of visible light measured at 400 nanometers wavelength. The basecoat compositions were made by blending a solvent-based basecoat, ODCT6505 (commercially available from PPG Industries, Inc.) with the same solvent-based clear basecoat composition without the pigment in the ratios shown in Table 1 below.

TABLE 1

| % Transmission at 400 nm | % Pigment | Parts by Weight ODCT6505 | Parts by Weight of clear basecoat |
|---|---|---|---|
| 78 | 0 | 0 | 100 |
| 48 | 10 | 10 | 90 |
| 32 | 20 | 20 | 80 |
| 19 | 30 | 30 | 70 |
| <1 | 100 | 100 | 0 |

The clear basecoat had the composition shown in Table 2 below.

TABLE 2

| INGREDIENTS | Parts by Weight |
|---|---|
| Di-isobutyl ketone | 53.45 |
| Xylene | 53.45 |
| Methyl ethyl ketone | 11.84 |
| Methyl amyl ketone | 91.91 |
| Methanol | 19.17 |
| N-Butyl acetate | 32.75 |
| Microgel[1] | 61.72 |
| Bentone Paste[2] | 62.14 |
| Resimene CE-6526[3] | 172.90 |
| Acrylic Resin[4] | 32.69 |
| Acrylic Resin[5] | 87.49 |
| Polyester Resin[6] | 14.20 |
| Polyester Resin[7] | 48.29 |
| Catalyst[8] | 10.49 |

[1]Prepared as described in U.S. Pat. No. 4,147,688, example II.
[2]A bentone paste prepared from a mixture of 24.1 parts acrylic resin (0.4% propylene imine/1.3% tertiary dodecane thiol/9.8% hydroxyethyl acrylate/19.1% n-butyl methacrylate/1.9% methacrylic acid/19.6% ethylhexyl acrylate/17.7% methyl methacrylate/29.5% styrene/0.6% acrylic acid) 52.9% solids in a mixture of isobutyl alcohol, VM&P Naphtha and n-butyl acetate, 4.0 parts oxidized polyethylene (20% in xylene), 5.0 parts Bentone 34 available from Elementis Specialties, and 29.1 parts n-butyl acetate.
[3]Melamine formaldehyde resin available from Solutia, Inc.
[4]Hydroxy functional acrylic resin (18.5% n-butyl methacrylate/40% hydroxypropyl acrylate/0.5% methyl methacrylate/20% styrene/19% n-butyl acrylate/2% acrylic acid), 67.3% solids in a mixture of acetone, Aromatic 100 and Dowanol PM Acetate.
[5]Hydroxy functional acrylic resin (1.1% tertiary dodecane thiol/9.9% hydroxyethyl acrylate/19.3% n-butyl methacrylate/1.9% methacrylic acid/19.8% ethylhexyl acrylate/18.4% methyl methacrylate/26.7% styrene) 51.1% solids in a mixture of isobutyl alcohol, VM&P Naphtha and toluene.
[6]Condensation reaction product of hexahydrophthalic anhydride (42.5% of reactant solids) and neopentylglycol (57.5% of reactant solids).

TABLE 2-continued

| INGREDIENTS | Parts by Weight |
|---|---|

[7]Condensation reaction product of adipic acid (19.3% of reactant solids), hexahydrophthalic anhydride (30.5% of reactant solids) and hexanediol (50.1% of reactant solids).
[8]Di-isoproanolamine neutralized di-nonylnaphthalene disulfonic acid.

The basecoat compositions were spray applied to each of the electrocoated test panels to yield a basecoat dry film thickness of approximately 0.7 to 0.8 mils (17.8 to 20.3 microns). The applied basecoat was given a one minute ambient flash period. A solvent-based clearcoat, ODCT8000 (commercially available from PPG Industries, Inc.) was then spray applied to the basecoat to give a dry clearcoat thickness of 1.6 to 1.8 mils (40.6 to 45.7 microns). The test panels were then thermally cured at a temperature of 285° F. (141° C.) for 30 minutes.

Light transmission of the basecoat/clearcoat system was determined using cured free films applied at the dry film thickness described above using a Perkin-Elmer Lambda 9 scanning spectrophotometer with a 150 millimeter Lab Sphere integrating sphere. Data collection was accomplished with Perkin-Elmer UV WinLab software in accordance with ASTM E903.

Photodegradation resistance was evaluated as described above in accordance with ASTM G90-98 using EMMAQUA-NTW®, available through Atlas Weathering Services, Inc., DSET Laboratories of Phoenix, Ariz. The test panels were cooled by forced air convection to limit the increase in surface temperatures of the specimens to 10° C. above the maximum surface temperature when identically mounted specimens are exposed to direct sunlight at normal incidence at the same UV radiation ranging between wavelengths of 295 and 385 nanometers.

EMMAQUA-NTW® test panels were removed from exposure and examined for delamination resistance by cross hatch adhesion testing of the exposed panel at each interval of accumulated radiant energy shown in Table 3 below. Adhesion testing was conducted before and after each of the test panels had been exposed for 16 hours at 100% relative humidity at 100° F. (38° C.). Cross hatch adhesion testing was done in accordance with ASTM D3359-97, using a 2 mm cross hatch tool (Model PA-2056, available from BYK Gardner) and rated using a rating scale ranging from 0 to 10 where 10 was the best. Each panel was also evaluated for degradation value (DV) by the analytical method described below.

Figure 4:
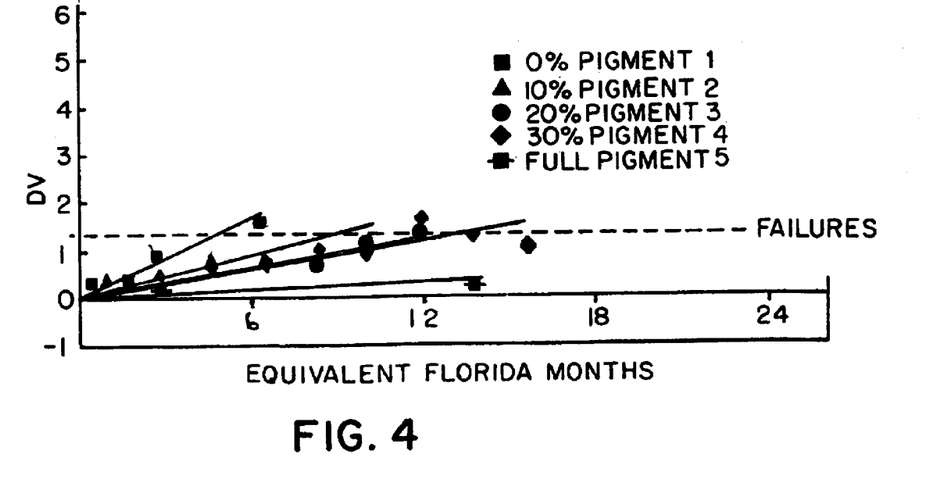
FIG. 4 is a graph of DV versus time for the procedure described in Example 1.

The radiant energy and cross hatch adhesion values are reported in Table 3 below. The "weeks" and "months" noted in Tables 3 and 4 and in FIG. 4 are "Equivalent Florida Weeks" and/or "Equivalent Florida Months" as defined in U.S. patent applications Ser. Nos. 10/010,437 and 10/005, 830, herein incorporated by reference.

TABLE 3

Radiant Energy Exposure and Cross Hatch Adhesion Ratings

| % Pigment | EMMAQUA-Arizona exposure time 2 weeks Radiant energy 11.15 MJ/m2 @ (295–385 nm) Adhesion Initial/Post-humidity 2 weeks | EMMAQUA-Arizona exposure time 4 weeks Radiant energy 22.31 MJ/m2 @ (295–385 nm) Adhesion Initial/Post-humidity 4 weeks | EMMAQUA-Arizona exposure time 8 weeks Radiant energy 44.62 MJ/m2 @ (295–385 nm) Adhesion Initial/Post-humidity 8 weeks | EMMAQUA-Arizona exposure time 12 weeks Radiant energy 66.92 MJ/m2 @ (295–385 nm) Adhesion Initial/Post-humidity 12 weeks | EMMAQUA-Arizona exposure time 20 weeks Radiant energy 111.54 MJ/m2 @ (295–385 nm) Adhesion Initial/Post-humidity 20 weeks | EMMAQUA-Arizona exposure time 28 weeks Radiant energy 156.15 MJ/m2 @ (295–385 nm) Adhesion Initial/Post-humidity 28 weeks |
|---|---|---|---|---|---|---|
| 0% | 10/10 | 10/10 | 10/10 | 10/10 | 8/0 | 8/0 |
| 10% | 10/10 | 10/10 | 10/10 | 10/10 | 9/7 | 9/7 |
| 20% | 9/10 | 9/10 | 10/10 | 10/10 | 8/8 | 8/8 |
| 30% | 9/9 | 8/10 | 10/10 | 10/10 | 8/8 | 8/8 |
| 100% | 8/10 | 8/10 | 9/9 | 9/9 | | |

| % Pigment | EMMAQUA-Arizona exposure time 36 weeks Radiant energy 200.77 MJ/m2 @ (295–385 nm) Adhesion Initial/Post-humidity 36 weeks | EMMAQUA-Arizona exposure time 44 weeks Radiant energy 245.38 MJ/m2 @ (295–385 nm) Adhesion Initial/Post-humidity 44 weeks | EMMAQUA-Arizona exposure time 52 weeks Radiant energy 290.00 MJ/m2 @ (295–385 nm) Adhesion Initial/Post-humidity 52 weeks | EMMAQUA-Arizona exposure time 60 weeks Radiant energy 334.61 MJ/m2 @ (295–385 nm) Adhesion Initial/Post-humidity 60 weeks | EMMAQUA-Arizona exposure time 68 weeks Radiant energy 379.23 MJ/m2 @ (295–385 nm) Adhesion Initial/Post-humidity 68 weeks | EMMAQUA-Arizona exposure time 76 weeks Radiant energy 423.85 MJ/m2 @ (295–385 nm) Adhesion Initial/Post-humidity 76 weeks |
|---|---|---|---|---|---|---|
| 0% | | | | | | |
| 10% | 10/4 | 7/0 | | | | |
| 20% | 9/7 | 8/7 | 10/8 | 8/2 | 10/0 | |
| 30% | 10/7 | 8/7 | 10/7 | 9/7 | 9/0 | 8/0 |
| 100% | | | | 10/9 | | |

Sample Preparation—Microtome Wedge Sections.

To obtain DV data, ultra low angle microtome wedge sections were obtained from intact coating systems and analyzed by Infrared microscopy. Microtome sections were obtained by adhering a panel section to the stage of a Leica SM2500E sledge microtome and then cut at a shallow angle. The advantage of this preparation technique is that it allows for the collection of thin sections containing coating layers of exaggerated thickness. Panel sections were approximately 2"×1" (5 cm by 2.5 cm) in size and the microtome stage was tilted at an angle of greater than 0° up to 5° from level to achieve a wedge cut. The panel section was adhered to the microtome stage using double-sided tape. During the cutting process, thin sections were collected until all of the individual coating layers were exposed. The thin sections used for analysis contained all of the coating layers of interest. The microtome thin sections were obtained at a thickness of 6 microns.

Analysis was performed by supporting the microtome thin sections on the stage of a Perkin Elmer Autoimage Infrared Microscope. The microscope aperture was oriented parallel to the coating system and set to a width of 200 microns and a height of 30 microns. Infrared transmission spectra were collected at the upper most surface region of the coating layer of interest (i.e. electrocoat, primer surfacer, etc.) and reference to air. The resulting spectrum was used to generate DV data.

After the IR spectra were obtained, the OH, NH and CH regions of the spectrum were integrated and the ratio of OH, NH to CH areas calculated. The initial ratio value, taken from an unexposed coating system (t=0), was subtracted from the value at a subsequent time (t=x), as shown in the equation below. The delta change represents the degradation value (DV) and this was then plotted versus exposure time. The slope of this line represents the degradation rate of the electrocoat or primer layers.

$$DV = \left[\frac{OH, NH}{CH}\right]_{t=x} - \left[\frac{OH, NH}{CH}\right]_{t=0}$$

A summary of the DV data from the current example appears in the Table 4 below.

TABLE 4

| | 0% Pigment | 10% Pigment | 20% Pigment | 30% Pigment | 100% Pigment |
|---|---|---|---|---|---|
| Control (unexposed) | 0 | 0 | 0 | 0 | 0 |
| 2 week (11.12 MJ/m2) | 0.33 | 0.27 | 0.21 | 0.21 | 0.08 |
| 4 week (22.31 MJ/m2) | 0.30 | 0.47 | 0.18 | 0.28 | 0.19 |
| 8 week (44.62 MJ/m2) | 0.44 | 0.35 | 0.27 | 0.15 | 0.13 |
| 12 week (66.92 MJ/m2) | 0.84 | 0.51 | 0.22 | 0.18 | 0.16 |
| 20 week (111.54 MJ/m2) | 1.39 | 0.84 | 0.62 | 0.63 | — |
| 28 week (156.15 MJ/m2) | 1.65 | 0.81 | — | 0.64 | — |
| 36 week (200.77 MJ/m2) | — | 0.81 | 0.67 | 1.03 | — |

TABLE 4-continued

|  | 0% Pigment | 10% Pigment | 20% Pigment | 30% Pigment | 100% Pigment |
|---|---|---|---|---|---|
| 44 week (245.38 MJ/m2) | — | 1.79 | 1.17 | 0.94 | — |
| 52 week (290 MJ/m2) | — | — | 1.38 | 1.62 | — |
| 60 week (334.61 MJ/m2) | — | — | 1.27 | 1.26 | 0.24 |
| 68 week (379.23 MJ/m2) | — | — | — | 1.11 | — |

All of these topcoat systems, independent of their pigment concentration, failed by delamination to the conventional electrocoat layer at approximately the same DV value. This is indicated in the graph of the DV data vs. exposure time shown in FIG. 4. Therefore, fully pigmented failure times can be predicted from short term exposures of unpigmented systems.

It will be readily appreciated by those skilled in the art that modifications may be made to the invention without departing from the concepts disclosed in the foregoing description. Accordingly, the particular embodiments described in detail herein are illustrative only and are not limiting to the scope of the invention, which is to be given the full breadth of the appended claims and any and all equivalents thereof.

What is claimed is:

1. A method of estimating the durability of a composite structure, comprising the steps of:
    a) providing a first composite structure comprising a plurality of layers including at least one under layer;
    b) obtaining samples of at least a portion of the under layer of the first composite structure over time by low angle microtoming;
    c) examining the samples from step b) to determine a degradation rate of the first composite structure;
    d) providing a second composite structure comprising a plurality of layers includino at least one under layer;
    e) obtaining samples of at least a portion of the under layer of the second composite structure over time by low angle microtoming;
    f) examining the samples from step e) to determine a degradation rate of the second composite structure; and
    g) comparing the degradation rate of the second composite structure to the degradation rate of the first composite structure.

2. The method of claim 1, wherein the first composite structure layers comprise a substrate and a polymeric coating comprising the at least one under layer and at least one outer layer.

3. The method of claim 2, wherein the examining step c) includes determining a degradation rate of the under layer of the first composite structure.

4. The method of claim 2, wherein the second composite structure layers compnse a substrate and a polymeric coating comprising the at least one under layer and at least one outer layer.

5. The method of claim 4, wherein the under layer of the first or second composite structure is an electrodeposited layer.

6. The method of claim 1, wherein examining steps c) and f) include obtaining infrared spectra comprising OH, NH, and CH regions of the at least one under layer of the first or second composite structures.

7. The method of claim 1, including:
    defining a failure value for the first composite structure; and
    calculating a time until the second composite structure reaches the failure value based on the degradation rate of the second composite structure.

8. The method of claim 1, wherein the second composite structure is processed under different processing parameters than the first composite structure.

9. A method of estimating the durability of a composite structure, comprising the steps of:
    a) providing a first composite structure comprising at least one under layer and at feast one outer layer;
    b) obtaining samples of at least a portion of the first composite structure over time by low angle microtoming, the samples including at least a portion of the under layer;
    c) examining the under layer portions of the samples from step b) to determine a degradation rate of the under layer;
    d) providing a second composite structure comprising at least one under layer and at least one outer layer;
    e) obtaining samples of at least a portion of the second composite structure over time by low angle microtoming, the samples including at least a portion of the under layer;
    f) examining the under layer portions of the samples from step e) to determine a degradation rate of the under layer of the second composite structure; and
    g) comparing the degradation rate of the second composite structure to the degradation rate of the first composite structure.

10. The method of claim 9, wherein the first and second composite structures include polymeric coating layers.

11. The method of claim 9, including:
    defining a failure value for the first composite structure; and
    calculating a time until the second composite structure reaches the failure value based on the degradation rate of the second composite structure.

12. The method of claim 9, wherein the second composite structure is different than the first composite structure.

13. The method of claim 9, wherein the second composite structure is processed under different processing parameters than the first composite structure.

14. The method of claim 9, wherein the first composite structure comprises:
    an electrodeposited under layer; and
    a topcoat.

15. The method of claim 14, wherein the electrodeposited under layer includes at least one pigment.

16. The method of claim 14, wherein the topcoat is deposited directly on the electrodeposited under layer.

17. The method of claim 14, wherein the topcoat comprises a basecoat and a clearcoat.

18. The method of claim 9, wherein the examining step c) comprises:
    conducting a low angle microtome of at least a portion of the first composite structure to obtain a sample containing at least a portion of the under layer; and
    analyzing the under layer portion of the sample.

19. The method of claim 18, wherein the analyzing step includes infrared microscopy.

20. The method of claim 19, wherein the analyzing step includes:

measuring an infrared spectrum of the under layer sample comprising OH, NH, and OH peak values;

integrating the OH, NH, and OH peak values; and calculating a ratio of the OH, NH to CH areas at a time value to obtain a degradation value.

21. The method of claim 20, wherein the examining step c) includes:

determining the degradation values of the first composite structure at a plurality of time values; and plotting the degradation values versus the time values to provide a degradation slope.

* * * * *